United States Patent [19]

Habeeb et al.

[11] 4,456,509

[45] Jun. 26, 1984

[54] METHOD OF PREPARING METAL DITHIOBENZOATES (PNE-361)

[75] Inventors: Jacob J. Habeeb, Sarnia, Canada; Keith Coupland, South Cliffe, England

[73] Assignee: Exxon Research and Engineering Co., Florham Park, N.J.

[21] Appl. No.: 395,596

[22] Filed: Jul. 6, 1982

[51] Int. Cl.³ .............................................. C25C 1/00
[52] U.S. Cl. ................................................. 204/59 R
[58] Field of Search ..................................... 204/59 R

[56] References Cited

U.S. PATENT DOCUMENTS

| | | | |
|---|---|---|---|
| 3,051,636 | 8/1962 | Kaspaul | 204/92 |
| 3,546,082 | 12/1970 | Mansfield | 204/72 |
| 3,556,960 | 1/1971 | McKeever et al. | 204/59 |
| 3,557,194 | 1/1971 | Fuchsman et al. | 260/502.6 |
| 3,964,983 | 6/1976 | Eisenbach | 204/59 R |

OTHER PUBLICATIONS

T. Roberie et al., "Complexes of Dithiobenzoic Acids, I. Preparation and Properties of a Series of Molybdenum (IV) Compounds" J. Coord. Chem., 9, 79, 1979.

J. P. Fackler, Jr. et al., "Sulfur Chelates VIII, Oxidative Addition of Sulfur to Dithioaryl Acid Complexes of Nickel (II) and Zinc (II)," J. Amer. Chem. Soc. 90:11, 2784, 1968.

G. K. Kohn, "Insecticidal 3,5-di-tert-4-hydroxybenzoates and thio derivatives" Chem. Abs., 13077d, 25-Noncondensed Aromtic, 80, 1974.

*Primary Examiner*—John F. Niebling
*Attorney, Agent, or Firm*—Eugene Zagarella

[57] ABSTRACT

This invention involves the preparation of selected metal dithiobenzoates by electrolysis of a substituted dithiobenzoic acid with a metal. It further involves the use of such metal dithiobenzoates as additives in lubricating hydrocarbon compositions.

6 Claims, No Drawings

METHOD OF PREPARING METAL DITHIOBENZOATES (PNE-361)

BACKGROUND OF THE INVENTION

This invention relates to a method for preparing selected metal dithiobenzoates and the use of such compounds as additives in lubricating hydrocarbon compositions.

A wide number of compounds have been disclosed as useful additives for lubricating compositions to reduce oxidative or thermal degradation, to reduce wear and to minimize rust, corrosion and friction. Some of the representative types of additives used in lubricating compositions are noted in "Lubricant Additives" by C. V. Smalheer and R. K. Smith, 1967.

One particular family of compounds which has found extensive use as antiwear and antioxidant additives in lubricating compositions is the metal dialkyldithiophosphates. While these compounds and other related compounds have excellent properties, certain types of applications require or prefer the use of additives where there is no phosphorus content.

While there are known additives which do not contain phosphorus, it has been difficult to find any having the overall effectiveness of the metal dialkyldithiophosphates.

SUMMARY OF THE INVENTION

Now in accordance with this invention a method has been found for preparing selected metal dithiobenzoates by electrolysis and such compounds have been found to be particularly useful as additives in lubricating hydrocarbon compositions.

DETAILED DESCRIPTION OF THE INVENTION

This invention is directed to the preparation and use of selected metal dithiobenzoates. More particularly, this invention involves the electrolysis of selected substituted dithiobenzoic acid with a chosen metal to form metal dithiobenzoates. Such prepared metal dithiobenzoates have the following general formula:

$$[\phi C(S)S]_2 M \qquad (I)$$

where 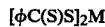 $\phi$ is the following group:

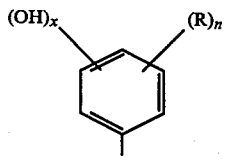

where R is an alkyl group of 1 to 18 carbons, preferably 1 to 6, n is an integer of 0, 1 or 2 and x is an integer of 0 or 1. Preferred compounds are x being 1, n being 2 with the OH in the para or 4 position from the open branch and the R groups being on both sides of the OH or in the 3, 5 positions.

The metal M found in compounds (I) can be essentially any of the metals of the Periodic Table and more particularly all of the transition metals as well as any of the metals of Groups IA to VA in the Periodic Table. The especially useful metals are Na, Mg, Ca, Ti, V, Cr, Mn, Fe, Co, Ni, Cu, Zn, Ga, Zr, Mo, Ag, Cd, In, Sn, Hf, W and Au with the particularly preferred metals being zinc (Zn), molybdenum (Mo) and magnesium (Mg). The metals, as noted above, are listed in the Periodic Table found in Lange's Handbook of Chemistry, Eleventh Edition, 1973. The transition metals as noted in this table include those found in Groups Ib to VIIb and VIII.

One problem associated with the preparation of the above type compounds (I) is the difficulty in obtaining the dithio compound from the perthio derivative because of the instability of the system. Other attempts to prepare the dithiobenzoates directly from metals, using conventional routes, gave either very low yields or failed completely due to the fast decomposition of the dithiobenzoic acid in a non neutral solvent medium. Now the dithiobenzoates (I) can be prepared in accordance with this invention by direct anodic dissolution of the selected metal with the substituted dithiobenzoic acid.

The desired dithiobenzoic acid can be obtained by reacting the selected starting material e.g. 2, 6 di-tert.-butyl phenol with carbon disulfide in an appropriate solvent system.

The dithiobenzoic acid starting material is then converted to the metal dithiobenzoate by electrolysis. This involves the direct anodic dissolution of the metal in a solution of the dithiobenzoic acid. Further details of a typical method of preparing the metal dithiobenzoates will be found in the examples.

The metal dithiobenzoates (I) prepared in accordance with the method of this invention have particular utility as additives in hydrocarbon compositions such as lubricating oils because of their antiwear, antioxidant and anticorrosion properties as well as heat and hydrolytic stabilities as typified in the examples that follow.

The hydrocarbon compositions in which the metal dithiobenzoates (I) can be used as additives include the mineral lubricating oils and the synthetic lubricating oils and mixtures thereof. The synthetic oils will include diester oils such as di-(2-ethylhexyl) sebacate, azelate and adipate; complex ester oils such as those formed from dicarboxylic acids, glycols and either monobasic acids or monohydric alcohols; silicone oils; sulfide esters; organic carbonates; and other synthetic oils known to the art. Further description of lubricating oils useful as base compositions may be found in Kirk-Othmer, Encyclopedia of Chemical Technology, 2nd Edition, Vol. 12, 1967, pp 557 to 616.

The base hydrocarbon composition will make up a major portion by weight of the composition of this invention with the metal dithiobenzoates (I) comprising an effective additive amount, i.e. stabilizing or inhibitive amount. More particularly, the metal dithiobenzoates will comprise from about 0.0001 to about 5.0 percent by weight and preferably from about 0.001 to about 1.0 percent by weight based on the total weight of the composition.

Other conventional type additives may be added to the hydrocarbon composition containing metal dithiobenzoates (I) in accordance with this invention depending on the particular application of said composition. Typical additives are disclosed in "Lubricant Additives" by C. Smalheer et al, described above.

The following examples are further illustrative of this invention and are not intended to be construed as limitations thereof.

EXAMPLE I

The compound 4-hydroxy-3,5-di-tert.-butyl dithiobenzoic acid was prepared by dissolving 2, 6-di-tert.-butyl phenol (20.6 g) in dimethylsulfoxide (60 cm$^3$). To this well stirred solution under a nitrogen blanket was added KOH (5.6 g) dissolved in a minimum amount of water. After the addition was completed carbon disulfide (7.6 g) was added while maintaining the temperature between 20°-25° C. The mixture was maintained at this temperature for 1 hour, then at 60° C. for 2 hours, cooled and poured into water (250 cm.$^3$). After acidification (10% HCl), extraction into diethyl ether and drying over Na$_2$SO$_4$ the product was isolated by rotoevaporation.

Zinc bis (4-hydroxy-3,5-di-tert.-butyl dithiobenzoate) was prepared as follows. The acid, 4-hydroxy-3,5-di-tert.-butyl dithiobenzoic acid (0.4 g) was dissolved in 15 ml. of methanol. Zinc wire (1.2 cm$^2$) as made the anode and platinum wire (1.4 cm$^2$) was made the cathode. The methanol/acid mixture was placed in a container housing the wire electrodes and 0.1 g of zinc metal was dissolved in 12 hours using 70 ma current and 12 volts. The resulting zinc bis (4-hydroxy-3,5-di-tert.butyl dithiobenzoate) was isolated from ether solution.

EXAMPLE II

The usefulness of the metal dithiobenzoates of this invention as additives in lubricating oil compositions is shown by the following antiwear, antioxidant, hydrolytic and heat stability tests carried out on representative lubricating oils containing the compound prepared in Example I. Table I through IX show the various test results.

TABLE I

ANTIWEAR PROPERTIES OF ZINC DITHIOBENZOATE IN LUBRICATING OIL FORMULATION: NORMAL FOUR-BALL WEAR TEST (ASTM D 2783)

| Load (kg)[2] | Scar Diameter (mm) | |
|---|---|---|
| | Lubricating Oil[1] Containing 1.934 wt % ZDDP[3] | Lubricating Oil[1] with 0.06 wt % ZDTB[4] and no ZDDP |
| 40 | 0.491 | 0.447 |
| 50 | 0.562 | 0.464 |
| 60 | 0.660 | 0.544 |
| 70 | 0.796 | 1.358 |

[1]Lubricating Oil: Fully formulated SAE grade 30 crankcase lube oil.
[2]Conditions: Speed 1200 rpm, temperature 65° C. and time 30 minutes.
[3]ZDDP: Zinc dialkyl dithiophosphate with a mixture of C$_4$ and C$_6$ alkyl groups.
[4]ZDTB: Zinc bis-(4-hydroxy-3,5-di-tert.-butyl dithiobenzoate).

TABLE II

ANTIWEAR PROPERTIES OF ZINC DITHIOBENZOATE IN LUBRICATING OIL FORMULATION: NORMAL FOUR-BALL WEAR TEST (ASTM D 2783)

| Load (kg)[2] | Scar Diameter (mm) | |
|---|---|---|
| | Lubricating Oil[1] Containing 1.934 wt % ZDDP[3] | Lubricating Oil[1] with 0.20 wt % ZDTB[4] and no ZDDP |
| 40 | 0.491 | 0.408 |
| 50 | 0.562 | 0.475 |
| 60 | 0.660 | 0.529 |
| 70 | 0.813 | 0.748 |
| 80 | 1.44 | 1.537 |

[1]Lubricating Oil: Fully formulated SAE grade 30 crankcase lube oil.
[2]Conditions: Speed 1200 rpm, temperature 65° C. and time 30 minutes.
[3]ZDDP: Zinc dialkyl dithiophosphate with a mixture of C$_4$ and C$_6$ alkyl groups.
[4]ZDTB: Zinc bis-(4-hydroxy-3,5-di-tert.-butyl dithiobenzoate).

TABLE III

ANTIWEAR PROPERTIES OF ZINC DITHIOBENZOATE IN LUBRICATING OIL FORMULATION: NORMAL FOUR-BALL WEAR TEST (ASTM D 2783)

| Load (kg)[2] | Scar Diameter (mm) | |
|---|---|---|
| | Lubricating Oil[1] Containing 1.953 wt % ZDDP[3] | Lubricating Oil[1] with 0.25 wt % ZDTB[4] and no ZDDP |
| 40 | 0.434 | 0.446 |
| 50 | 0.520 | 0.508 |
| 60 | 0.689 | 0.544 |
| 70 | 0.900 | 0.792 |

[1]Lubricating Oil: Fully formulated heavy duty SAE grade 10 crankcase lube oil.
[2]Conditions: Speed 1200 rpm, temperature 65° C. and time 30 minutes.
[3]ZDDP: Zinc dialkyl dithiophosphate with a mixture of C$_4$ and C$_6$ alkyl groups.
[4]ZDTB: Zinc bis-(4-hydroxy-3,5-di-tert.-butyl dithiobenzoate).

TABLE IV

ANTIOXIDANT PROPERTIES OF ZINC DITHIOBENZOATE IN ERE OXIDATION TEST[2]

| Formulation | Viscosity @ 40° C., cST | | Total Base No., mg KOH/g oil | | Total Acid No., mg KOH/g oil | | wt of Cu loss, g |
|---|---|---|---|---|---|---|---|
| | Before | After | Before | After | Before | After | |
| 1. Lubricating Oil[1] containing 1.934 wt % of ZDDP[3] | 122.3 | 148.0 | 2.22 | NIL | 3.38 | 9.25 | 0.0037 |
| 2. Lubricating Oil[1] without ZDDP | 122.0 | 357.9 | 2.35 | NIL | 1.65 | 10.50 | 0.0932 |
| 3. As in 2 + 0.034 wt % ZDTB[4] | 121.9 | 259.8 | 2.41 | NIL | 1.70 | 1.68 | 0.1363 |
| 4. As in 2 + 0.060 wt % ZDTB[4] | 123.9 | 198.8 | 3.00 | 0.01 | 1.38 | 0.57 | 0.1200 |
| 5. As in 2 + 0.20 wt % ZDTB[4] | 122.6 | 169.2 | 2.54 | NIL | 2.41 | 11.87 | 0.0086 |

[2]Conditions: Temperature 172° C. and time 23 hours
[1], [3], [4]Same as in Tables I and II

TABLE V

HYDROLYTIC STABILITY (ASTM D2619) RESULTS FOR ZINC DITHIOBENZOATE CONTAINING FORMULATIONS

| | Additives Added to Lubricating Oil Formulation[1] [2] | | |
|---|---|---|---|
| | Spec | ZDDP[3] 0.057 wt % Zn | ZDTB[4] 0.01 wt % Zn (0.1 wt % ZDTB) |
| Cu Loss, mg/cm$^2$ | 0.2 Max | 4.5 | 0.07 |
| H$_2$O Acidity, mg KOH | 4.0 Max | 0.1 | 0.10 |

[1]Lubricating Oil: Fully formulated industrial hydraulic oil.
[2]Conditions: 48 hours and 93° C. (200° F.).
[3]ZDDP: Zinc dialkyl dithiophosphate with a mixture of C$_4$ and C$_6$ alkyl groups.
[4]ZDTB: Zinc bis-(4-hydroxy-3,5-di-tert.-butyl dithiobenzoate).

TABLE VI

CINCINNATI MILACRON[2] HEAT STABILITY RESULTS FOR LUBRICATING OIL FORMULATION CONTAINING ZINC DITHIOBENZOATE

| | Additives Added to Lubricating Oil Formulation[1] [2] | | |
|---|---|---|---|
| | Spec | ZDDP[3] 0.057 wt % Zn | ZDTB[4] 0.01 wt % Zn (0.1 wt % ZDTB) |
| Cu Loss, mg/200 ml | 10 Max | 27.6 | 8.0 |
| Sludge, mg/100 ml | 100 Max | 240.2 | 10.4 |

[1] Lubricating Oil: Fully formulated industrial hydraulic oil.
[2] 168 hrs and 135° C. (Publication No. 10-SP-7421-3)
[3] ZDDP: Zinc dialkyl dithiophosphate with a mixture of $C_4$ and $C_6$ alkyl groups.
[4] ZDTB: Zinc bis-(4-hydroxy-3,5-di-tert.-butyl dithiobenzoate).

TABLE VII

ANTIOXIDANT PROPERTIES OF ZINC DITHIOBENZOATE IN NEW MODIFIED INDIANA TEST[1]

| Formulation | Viscosity at 100° C., cSt | | Cold-Cranking Simulator, poise | |
|---|---|---|---|---|
| | Before | After | Before | After |
| 1. Lubricating Oil[2] containing 1.953 wt % ZDDP[3] | 6.1 | 8.2 | 25.0 | 48.7 |
| 2. Lubricating Oil[2] with 0.08 wt % ZDTB[4] and no ZDDP | 6.6 | 8.3 | 27.0 | 50.0 |
| 3. Lubricating Oil[2] with 0.25 wt % ZDTB[4] and no ZDDP | 6.1 | 7.7 | 24.8 | 44.9 |

[1] An industry wide oxidation test - Take 340 mls. oil at 160° C. with Fe powder (1000 ppm) as catalyst for 72 hrs. with air blown in at a rate of 3.8 ft$^3$/hr.
[2] Lubricating Oil: Fully formulated heavy duty SAE grade 10 crankcase lube oil.
[3] ZDDP: Zinc dialkyl dithiophosphate with a mixture of $C_4$ and $C_6$ alkyl groups.
[4] ZDTB: Zinc bis-(4-hydroxy-3,5-di-tert.-butyl dithiobenzoate).

TABLE VIII

VICKERS VANE PUMP TEST[1] RESULTS OF ZINC DITHIOBENZOATE IN LUBRICATING OIL FORMULATION[2]

| Antioxidant-Antiwear Additive | Zn, wt % | Cumulative Wt Loss, mg |
|---|---|---|
| ZDDP[3] (1.78 wt %) | 0.14 | 63.6 |
| ZDTB[4] (1.05 wt %) | 0.11 | 72.4 |

[1] Test Conditions: Pump pressure 140.62 Kg/cm$^2$; Temperature 79° C.; Time 100 hours; Pump rate 23.64 L/minutes (ZDDP[3]); 11.82 L/minutes (ZDTB[4]), ASTM D 2882.
[2] Lubricating Oil: Multigrade fully formulated 5W30 heavy duty crankcase oil.
[3] ZDDP: zinc dialkyl dithiophosphate with $C_8$ alkyl groups.
[4] ZDTB: zinc bis(4-hydroxy-3,5-di-tert.-butyl dithiobenzoate).

TABLE IX

L-38 RESULTS OF ZINC DITHIOBENZOATE IN LUBRICATING OIL FORMULATION[1] [2]

| Antiwear-Antioxidant | Zn, wt % | Bearing Weight Loss, mg |
|---|---|---|
| ZDDP[3] (1.78 wt %) | 0.14 | 18.9 |
| ZDTB[4] (1.06 wt %) | 0.11 | 18.2 |

[1] Labcco L-38 test method, ASTM STP 509A, Part IV - an engine test to examine the oxidation, sludge formation, corrosion and varnish of crankcase oils.
[2] Lubricating oil: Multigrade fully formulated 5W30 heavy duty crankcase oil.
[3] ZDDP: zinc dialkyl dithiophosphate with $C_8$ alkyl groups.
[4] ZDTB: zinc bis(4-hydroxy-3,5-di-tert.-butyl dithiobenzoate).

What is claimed is:

1. A method for preparing metal dithiobenzoates having the formula $[\phi C(S)S]_2 M$ where M is a transition metal or metal of Groups IA to VA of the Periodic Table and $\phi$ is the following group:

$$(OH)_x \diagup \diagdown (R)_n \qquad (I)$$

where R is an alkyl of 1 to 18 carbons, n is 0, 1 or 2 and x is 0 or 1, comprising electrolyzing said metal with a substituted dithiobenzoic acid, said acid having substituents as in the above group (I).

2. The method of claim 1 wherein said metal is zinc, molybdenum, or magnesium.

3. The method of claim 2 where R is an alkyl of 1 to 6 carbons.

4. The method of claim 3 where n is 2 and x is 1.

5. The method of claim 4 where the OH group is in the para position to the acid group and the R groups are in the 3, 5 position relative to the acid group.

6. The method of claim 5 wherein the R groups are tert.-butyl.

* * * * *